US008993546B2

(12) United States Patent
Blakely et al.

(10) Patent No.: US 8,993,546 B2
(45) Date of Patent: Mar. 31, 2015

(54) PARASITICIDAL COMPOSITION

(75) Inventors: William Blakely, County Down (GB); Lillian Cromie, County Down (GB)

(73) Assignee: Norbrook Laboratories Limited (GB)

(*) Notice: Subject to any disclaimer, the term of this patent is extended or adjusted under 35 U.S.C. 154(b) by 1293 days.

(21) Appl. No.: 11/330,671

(22) Filed: Jan. 12, 2006

(65) Prior Publication Data

US 2006/0142216 A1  Jun. 29, 2006

Related U.S. Application Data

(63) Continuation-in-part of application No. PCT/GB2004/003006, filed on Jul. 12, 2004.

(30) Foreign Application Priority Data

Jul. 12, 2003 (GB) .................................. 0316377.1

(51) Int. Cl.
*A01N 37/36* (2006.01)
*A61K 45/06* (2006.01)
*A01N 37/40* (2006.01)
*A61K 31/045* (2006.01)
*A61K 31/609* (2006.01)

(52) U.S. Cl.
CPC ................ *A61K 45/06* (2013.01); *A01N 37/40* (2013.01); *A61K 31/045* (2013.01); *A61K 31/609* (2013.01)
USPC ......................................... 514/166; 424/405

(58) Field of Classification Search
USPC .......................................... 424/405; 514/166
See application file for complete search history.

(56) References Cited

U.S. PATENT DOCUMENTS

| 2,731,386 | A | * | 1/1956 | Reiner | 514/160 |
|---|---|---|---|---|---|
| 3,798,258 | A | * | 3/1974 | Patchett et al. | 564/166 |
| 3,862,305 | A | * | 1/1975 | Bouillon et al. | 424/45 |
| 5,516,761 | A | * | 5/1996 | Choi et al. | 514/30 |
| 5,840,324 | A | * | 11/1998 | Hennessy et al. | 424/418 |
| 6,239,119 | B1 | * | 5/2001 | Stogniew et al. | 514/131 |
| 6,492,340 | B2 | | 12/2002 | Mihalik | 514/30 |
| 6,492,419 | B1 | * | 12/2002 | Shepherd | 514/549 |
| 7,238,680 | B2 | * | 7/2007 | Rosen | 514/165 |
| 2002/0010142 | A1 | * | 1/2002 | Mihalik | 514/30 |
| 2002/0035076 | A1 | * | 3/2002 | Parks | 514/28 |

FOREIGN PATENT DOCUMENTS

| AU | 2003275779 B2 | 6/2004 |
|---|---|---|
| GB | 2 386 067 | 9/2003 |
| GB | 2 386 067 A | 9/2003 |
| GE | 2490 | 7/2001 |
| RU | 2033150 | 4/1995 |
| RU | 95122150 | 2/1998 |
| RU | 97112506 | 2/1999 |
| RU | 2129430 | 4/1999 |
| WO | WO-95/05812 | 3/1995 |
| WO | WO 95/05812 | 3/1995 |
| WO | WO 97/13508 | 4/1997 |
| WO | WO-97/13508 | * 4/1997 |
| WO | WO-00/04906 | 2/2000 |
| WO | WO 00/04906 | 2/2000 |
| WO | 2001/060380 A1 | 8/2001 |
| WO | WO 02/09764 | 2/2002 |
| WO | WO 2004/043445 | 5/2004 |
| WO | WO 2004/069242 | 8/2004 |

OTHER PUBLICATIONS

Lau et al., "Antihelmintic Composition", Aug. 19, 2004, International Application Published Under the PCT, WO 2004/069242 A1.*
Razzak et al., "Combination Compositions", Feb. 7, 2002, International Application Published Under the PCT, WO 02/09764 A1.*
Search Report from the National Centre of the Intellectual Property "Sakpatenti"of Georgia, No. 37944, dated Feb. 12, 2007, related to Georgian application AP 2004 009216 "Parasiticidal Composition" and an English translation.
Wisniewski, S.J. et al. An in vitro/in vivo comparison of a closantel sodium pour-on formulation in sheep, Proceedings of the International Symposium on Controlled Release of Bioactive Materials, 1977, 24$^{th}$ p. 741-742.
Response to Jul. 28, 2009 Examination Report for African Regional Intellectual Property Organization in connection with corresponding African Application No. AP/P/2006/003506 (dated Feb. 1, 2010).
Response to Feb. 23, 2010 Re-Examination Report for African Regional Intellectual Property Organization in connection with corresponding African Application No. AP/P/2006/003506 (dated Jun. 30, 2010).
Response to Office Action in connection with corresponding Cuban Application No. 1/2006 (Mar. 30, 2009).
Office Action received in connection with corresponding Cuban Application No. 1/2006 (dated Jan. 29, 2009).
First Office Action (English Translation) received in connection with corresponding Chinese Application No. 200480020006.X (received Jan. 14, 2008).

(Continued)

Primary Examiner — Ali Soroush
(74) Attorney, Agent, or Firm — Porzio, Bromberg & Newman P.C.

(57) ABSTRACT

An anti-parasiticidal composition presented as a topical "pour-on" product for treating animals infected by parasites which are known to be susceptible to salicylanilides, especially closantel, alone or together with at least one other anti parasitic compound of the avermectin or milbemycin type and offers enhanced bioavailability of the salicylanilide by provision of a delivery system comprising at least 20% (v/v) of one or more alcohols, and optionally including a polymeric moiety selected from the group consisting of polyvinylpyrrolidone (PVP), polyoxypropylene/polyoxyethylene block copolymers (poloxamer), and polyethylene glycols (PEG), thereby improving the bioavailability of e.g. closantel (as assessed with respect to blood plasma levels of closantel).

15 Claims, 1 Drawing Sheet

(56) References Cited

OTHER PUBLICATIONS

Second Office Action (and English Translation) received in connection with corresponding Chinese Application No. 200480020006.X (received Jul. 2, 2009).
Third Office Action (English Translation) received in connection with corresponding Chinese Application No. 200480020006.X (received Jan. 18, 2010).
Fourth Office Action (English Translation) received in connection with corresponding Chinese Application No. 200480020006.X (dated Jan. 6, 2011).
First Examination Report received in connection with corresponding Indian Application No. 675/DELNP/2006 (dated May 25, 2009).
Response to Opposition filed by the Association of Pharmaceutical Laboratories for corresponding Ecuador Application No. SP06-6360 (filed Aug. 16, 2007).
Notification on Result of Substantive Examination (and English Translation) received in connection with corresponding Vietnamese Application No. 1-2006-00201 (dated Jun. 10, 2010).
Official decision received in connection with corresponding Egyptian Application No. PCT 32/2006 (dated Oct. 9, 2010).
Response to Jan. 14, 2008 Office Action for Chinese Application No. 200480020006.X (Oct. 19, 2009).
Response to Jul. 2, 2009 Office Action for Chinese Application No. 200480020006.X (Feb. 23, 2010).
Response to Jan. 18, 2010 Office Action for Chinese Application No. 200480020006.X (Nov. 3, 2011).
Response to Jan. 6, 2011 Office Action for Chinese Application No. 200480020006.X (Mar. 12, 2012).
Request Re-Examination in connection with Chinese Application No. 200480020006.X (dated Apr. 20, 2011).
Examination report received in connection with United Kingdom Application No. GB0415541.2 (dated Aug. 24, 2005).
Response to Aug. 24, 2005 Examination report for United Kingdom Application No. GB0415541.2 (Oct. 6, 2005).
Combined Search and Examination Report received for United Kingdom Application No. GB0415541.2 dated 5 Nov. 2004.
Response to Nov. 5, 2004 Examination report for United Kingdom Application No. GB0415541.2 (Aug. 9, 2005).
Examination Report received in connection with corresponding European Patent Application No. 04743347.9 (dated Aug. 5, 2009).
Response to Aug. 5, 2009 Examination Report for corresponding European Patent Application No. 04743347.9 (Jan. 27, 2010).
Examination Report received in connection with corresponding European Patent Application No. 04743347.9 (dated Nov. 22, 2011).
Response to Nov. 22, 2011 Examination Report for corresponding European Patent Application No. 04743347.9 (Dec. 12, 2011).
First Examination Report and English Translation received in connection with corresponding Uzbekistanian Patent Application No. IAP20060013 (dated Mar. 29, 2007).
Second Examination Report and English Translation received in connection with corresponding Uzbekistanian Patent Application No. IAP20060013 (dated Sep. 26, 2007).
Third Examination Report and English Translation received in connection with corresponding Uzbekistanian Patent Application No. IAP20060013 (dated Mar. 28, 2008).
Fourth Examination Report (English Translation) received in connection with corresponding Uzbekistanian Patent Application No. IAP20060013 (dated Sep. 16, 2008).
Examination Report received in connection with corresponding Philippines Patent Application No. 1-2006-500104 (mailed May 29, 2009).
Response to Examination Report in connection with corresponding Philippines Patent Application No. 1-2006-500104 (dated Jul. 27, 2009).
Examination Report received in connection with corresponding ARIPO Patent Application No. AP/P/2006/003506 (dated Jul. 28, 2009).
Examination Report received in connection with corresponding ARIPO Patent Application No. AP/P/2006/003506 (dated Feb. 23, 2010).
Examination Report received in connection with corresponding ARIPO Patent Application No. AP/P/2006/003506 (dated Feb. 15, 2011).
The response which was filed to the documentary conclusion on defining of the state of art for corresponding Georgian Patent Application No. AP2004009216 dated Jul. 20, 2007.
Voluntary Amendment filed in connection with corresponding Canadian Patent Application No. 2532199 (Feb. 9, 2010).
Examiner's Report received in connection with corresponding Canadian Patent Application No. 2532199 (dated Feb. 4, 2011).
Response to Feb. 4, 2011 Examiner's Report for corresponding Canadian Patent Application No. 2532199 (Aug. 3, 2011).
Examiner's Report received in connection with corresponding Canadian Patent Application No. 2532199 (dated Nov. 10, 2011).
Response to Nov. 10, 2011 Examiner's Report for corresponding Canadian Patent Application No. 2532199 (Nov. 30, 2011).
Examination Report received in connection with corresponding Israeli Patent Application No. 173057 (dated Jul. 29, 2010).
Examination Report received in connection with corresponding New Zealand Patent Application No. 544973 (dated Mar. 10, 2008).
Response to Mar. 10, 2008 Examination Report for corresponding New Zealand Patent Application No. 544973 (Aug. 14, 2008).
Response claims to decision rejecting application in connection with corresponding Egyptian Application No. PCT 32/2006 (dated Mar. 15, 2010).
Examiner's First Report received in connection with corresponding Australian Patent Application No. 2004257450 (dated Jul. 18, 2007).
Response to Jul. 18, 2007 First Examiner's Report for corresponding Australian Patent Application No. 2004257450 (Jul. 31, 2008).
Invitation to Respond to Written Opinion, received in connection with corresponding Singapore Patent Application No. 200600197-8 (dated Aug. 28, 2007).
Response to Written Opinion dated Aug. 28, 2007, for corresponding Singapore Patent Application No. 200600197-8 (Jan. 25, 2008).
Examination Report for corresponding Singapore Patent Application No. 200600197-8 (dated May 20, 2008).
Documentary Conclusion on Defining of the State of Art (English Translation) for corresponding Georgian Patent Application No. AP2004009216 (dated Jul. 20, 2007).
First Office Action (English Translation) received in connection with corresponding Japanese Patent Application No. 2006-519991 (dated Aug. 17, 2010).
Office Action received in connection with corresponding Mexican Patent Application No. PA/A/2006/000135 (dated May 15, 2009).
European Search Report and Examination Report received in connection with corresponding European Patent Application No. 10012261.3 (dated Dec. 6, 2010).
Response to Feb. 28, 2011 Examination Report for corresponding European Patent Application No. 10012261.3 (Aug. 23, 2011).
Examination Report received in connection with corresponding Philippines Patent Application No. 1-2006-500104 (mailed Mar. 31, 2009).
Response to Examination Report in connection with corresponding Philippines Patent Application No. 1-2006-500104 (dated May 6, 2009).
Office Action and English Summary of Office Action received in connection with corresponding Korean Patent Application No. 10-2006-7000779 (mailed Feb. 22, 2011).
First Office Action received in connection with corresponding Chile Application No. 168-06 (received Feb. 13, 2008).
Response to Feb. 13, 2008 Office Action for Chile Application No. 168-06 (Sep. 24, 2008).
Second Office Action received in connection with corresponding Chile Application No. 168-06 (received Jan. 15, 2009).
First Office Action received in connection with corresponding Columbia Application No. 06013088 (dated Aug. 28, 2009).
Response to Aug. 28, 2009 Office Action for Columbia Application No. 06013088 (Nov. 20, 2009).
Second Office Action received in connection with corresponding Columbia Application No. 06013088 (dated Apr. 29, 2011).
Response to Apr. 29, 2011 Office Action for Columbia Application No. 06013088 (Jul. 26, 2011).

(56) References Cited

OTHER PUBLICATIONS

Third Office Action received in connection with corresponding Columbia Application No. 06013088 (dated Oct. 28, 2011).
Response to Oct. 28, 2011 Office Action for Columbia Application No. 06013088 (Jan. 24, 2012).
Resolution received in connection with corresponding Columbia Application No. 06013088 (dated Feb. 29, 2012).
Response to Feb. 29, 2012 Resolution in connection with corresponding Columbia Application No. 06013088 (dated Apr. 12, 2012).
First Examination Report (and English Translation) received in connection with corresponding Eurasian Patent Application No. 200600237 (dated Feb. 20, 2007).
Response to First Examination Report received in connection with corresponding Eurasian Patent Application No. 200600237 (dated Jun. 26, 2007).
Second Examination Report (and English Translation) received in connection with corresponding Eurasian Patent Application No. 200600237 (dated Jun. 26, 2007).
Response to Second Examination Report received in connection with corresponding Eurasian Patent Application No. 200600237 (dated Oct. 24, 2007).
Search Report (English Translation) for corresponding Georgian Patent Application No. AP2004009216 (dated Feb. 12, 2007).
Response to Search Report for corresponding Georgian Patent Application No. AP2004009216 (dated Jul. 20, 2007).
Response to First Examination Report in connection with corresponding Indian Application No. 675/DELPN/2006 (dated Mar. 5, 2010).
Second Examination Report received in connection with corresponding Indian Application No. 675/DELNP/2006 (dated Apr. 23, 2010).
Response to Second Examination Report received in connection with corresponding Indian Application No. 675/DELNP/2006 (dated May 25, 2010).
Response to Examiner Conference filed in connection with corresponding Indian Application No. 675/DELNP/2006 (dated Sep. 3, 2010).
Office Action received in connection with Indonesian Application No. W00.2006.00081 (dated Jul. 12, 2011).
Response to Office Action in connection with Indonesian Application No. W00.2006.00081 (dated Mar. 13, 2012).
Response to First Office Action in connection with corresponding Israeli Patent Application No. 173057 (dated Dec. 29, 2008).
Response to Second Office Action (and English Translation) in connection with corresponding Israeli Patent Application No. 173057 (dated Dec. 26, 2010).
Third Office Action received in connection with corresponding Israeli Patent Application No. 173057 (dated Dec. 26, 2011).
Response to Third Office Action in connection with corresponding Israeli Patent Application No. 173057 (dated May 16, 2012).
Notification Prior to Examination (English Translation) received in connection with corresponding Israeli Patent Application No. 173057 (dated Aug. 11, 2008).
Response to First Office Action and English translation of amended claims, in connection with corresponding Japanese Patent Application No. 2006-519991 (dated Nov. 17, 2010).
Response to Office Action in connection with corresponding Mexican Patent Application No. PA/A/2006/000135 (dated Jul. 28, 2009).
Technical Report with English translation in connection with corresponding application in Peru Application No. 000032-2006OIN (dated Feb. 5, 2009).
Response to First Office Action and English amended claims in connection with corresponding Korean Patent Application No. 10-2006-7000779 (Apr. 22, 2011).
Request for Examination in connection with corresponding Korean Patent Application No. 10-2006-7000779 (Jun. 8, 2009).
Response to Notification on Result of Substantive Examination received in connection with corresponding Vietnamese Application No. 1-2006-00201 (dated Jul. 23, 2010).
Response to First Examination Report in connection with corresponding Uzbekistanian Patent Application No. IAP20060013 (dated Jun. 27, 2007).
Response to Second Examination Report in connection with corresponding Uzbekistanian Patent Application No. IAP20060013 (dated Jan. 24, 2008).
Response to Third Examination Report in connection with corresponding Uzbekistanian Patent Application No. IAP20060013 (dated Jul. 28, 2008).
Response to Fourth Examination Report and allowed claims (English translation) in connection with corresponding Uzbekistanian Patent Application No. IAP20060013 (dated Dec. 15, 2008).
First Office Action received in connection with Egyptian Application No. PCT 32/2006 (dated Nov. 17, 2008).
Response to First Office Action in connection with corresponding Egyptian Application No. PCT 32/2006 (Jan. 2009).
Second Office Action received in connection with Egyptian Application No. PCT 32/2006 (dated Dec. 29, 2009).
Response to Second Office Action in connection with corresponding Egyptian Application No. PCT 32/2006 (Mar. 2010).
Schnieder et aL, "The efficacy of strategic treatments with ivermectin pour-on against trichostrongylid and lungworm infections in first year grazing calves in Northern Germany," Angew. Parasitol., vol. 32, pp. 185-192 (1991).
Search Report—Application No. GB0415541.2; Nov. 2, 2004.

\* cited by examiner

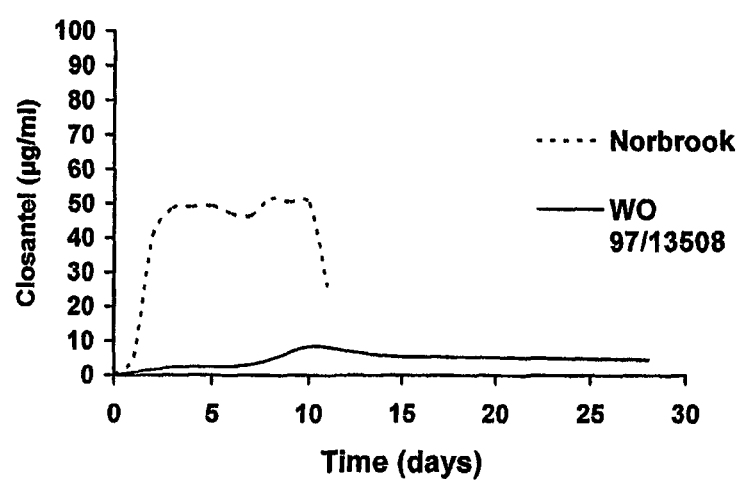

PARASITICIDAL COMPOSITION

CROSS REFERENCE TO RELATED APPLICATIONS

This application is a Continuation-in-Part of PCT International application no. PCT/GB2004/003006 filed Jul. 12, 2004 and published in English as WO 2005/007241 on Jan. 27, 2005, which claims the priority of British Patent No. 0316377.1, filed on Jul. 12, 2003. The disclosures of both are hereby incorporated herein by reference in their entirety.

FIELD OF THE INVENTION

This invention relates to parasiticidal compositions, especially combination products for veterinary use, based on a salicylanilide optionally together with another parasiticidal agent, for example an avermectin or milbemycin, Such combination products exhibit efficacy across a broader spectrum of parasites than is observed with the use of a single parasiticidal agent alone.

BACKGROUND OF THE INVENTION

Warm-blooded animals are subject to attack by parasites, and man has long sought to combat such parasites afflicting domestic companion animals, farmed livestock and exotic animals, to alleviate suffering and for commercial gain. The manner of attack by the parasites, and the identification of a sensitive stage in the life cycle of the parasite, may influence greatly the choice of combating agent. Thus percutaneous treatments using topically applied preparations such as lotions, paints, creams, gels, dusting powders, "pour-ons" and dips are commonly suitable for ectoparasites, but combating endoparasites requires careful selection of the method of administration and the delivery system. Oral drenches, pastes, boluses, tablets, and granules for incorporating into feed mixes are known methods capable of being used by the animal husbandrymen, but other methods which are intended to avoid use of the gastrointestinal route are typically administered by qualified practitioners. Such other methods include use of aerosols, and parenteral drug compositions which are selectively prepared as solution or suspension or micronised powder formulations intended for subcutaneous, intracutaneous, and intramuscular injection according to the intended delivery regime. These last methods require special care in formulation to avoid irritation at the site of injection or possible adverse allergic or pyrogenic reactions.

Formulations are typically prepared using aqueous or non-aqueous ("solvent") vehicles. The latter class may comprise physiologically tolerable alcohols, glycols, esters, a limited range of organic aromatic solvents, and vegetable oils and extracts or modified forms thereof. In selecting vehicles, the skilled worker has to consider a number of issues including, solubility of the intended active ingredient(s), the affinity of the drug to certain vehicles, whether it will affect any essential auxiliaries, pH, stability over time, viscosity, and naturally the risk of any toxic effect upon the animal to be treated. In the case of a "pour-on" formulation, the ability to facilitate the transfer of the active ingredient or ingredients through the skin and into the bloodstream to provide an efficacious dose is an essential feature of the composition. Therefore, formulation of a parasiticide is a complex task.

Traditional parasiticides include chemical agents such as the benzimidazoles, and carbamates, and plant extracts such as the pyrethroids, which tend to be used to combat ectoparasites such as ticks and mites.

The salicylanilides, tend to be effective against fungal attack, but the chemically modified derivative closantel is an effective worming agent. Closantel is described in U.S. Pat. No. 4,005,218 and in the literature, e.g. J. Guerrero et al, J. Parasitol. 68,616, (1983); H. Van den Bossche et al, Arch. Int. Physiol. Biochim, 87, 851(1979); H. J. Kane et al, Mol. Biochem. Parasitol. 1, 347(1980).

Closantel is typically administered by the oral route e.g. as a bolus, or oral drench, or parenterally as an injection solution. WO 95/05812 suggests that an injectable anthelmintic composition containing abamectin and closantel can be produced with glycerol formal optionally using a glycol-based solvent such as polyethylene glycol 400, or propylene glycol. However, because the topical route of administration is generally slower than any other routes (injection or oral route), absorption of closantel through the skin would be expected to be very slow, therefore closantel plasma levels would be expected to be lower than that obtained by delivery by any other route.

Closantel is also very hydrophobic and is very quickly and substantially bound to plasma proteins, this again would suggest to those skilled in the art that administration by topical means would reduce the achievable plasma concentration.

Therefore, currently there is no known commercial formulation adapted for administration of closantel as a pour-on.

The avermectins are very potent antiparasitic agents which are useful against a broad spectrum of endoparasites and ectoparasites in mammals as well as having agricultural uses against various parasites found in and on crops and soil. The basic avermectin compounds are isolated from the fermentation broth of the soil micro-organism *Streptomyces avermitilis* and these compounds are described in U.S. Pat. No. 4,310, 519. Furthermore, derivatives of these basic avermectin compounds have been prepared by a variety of chemical means.

Some of the avermectin group of compounds contain a 22,23-double bond and others contain a disaccharide at the 13-position which consists of α-L-oleandrosyl-α-L-oleandrosyl group. One or both saccharide units can be removed forming a monosaccharide or an aglycone (where both saccharides are removed) as described in U.S. Pat. No. 4,206, 205. The aglycone derivatives possess a hydroxy group at the 13 position which may be removed to form the 13-deoxy compound as described in the U.S. Pat. No. 4,171,314 and U.S. Pat. No. 4,173,571. Acylaton of hydroxy groups on the avermectin compounds and derivatives can be carried out as described in U.S. Pat. No. 4,201,861.

The milbemycin series of compounds, disclosed in U.S. Pat. No. 3,950,360, are structurally similar to the avermectin family in that they contain the sixteen membered macrocyclic ring. However, they do not contain the disaccharide sub-unit and there are differences in the substituent groups.

Ivermectin, disclosed in U.S. Pat. No. 4,199,569, is prepared by the selective reduction of the 22, 23 double bond of the avermectin compounds. Ivermectin is a mixture of 22,23-dihydro Avermectin B1a and B1b in a ratio of at least 80:20.

Ivermectin is an especially preferred active component in pesticidal compositions, and there is extensive literature on its activity, demonstrating its efficacy against internal and external parasites, and its ability to interfere in the life cycle of certain parasites. The Merck Index (1996) cites several references including J. C. Chabala et al, J. Med. Chem. 23, 1134 (1980); J. R. Egerton et al, Brit. Vet. J. 136, 88 (1980); W. C. Campbell et al, Science 221, 823-828 (1983) to mention but a few.

Formulation of ivermectin for the purposes of delivery in a variety of presentations, e.g. as an oral drench, pour-on, parenteral formulations, granules for adding to feed, and syringeable pastes has proved highly challenging and numerous patents have been published on its use. Ivermectin exhibits a lipophilic character but it can be solvated in aqueous systems, and various patents describe special solvent systems for use in its formulation. Thus reference may be made at least to EP 0 045 655, and EP 0 146 414 for example.

Although ivermectin is surprisingly effective, and has enjoyed a long period of commercial success, there remains a keen interest in exploiting ivermectin against a wider range of parasites and in overcoming tolerance by some parasites which demands higher amounts of ivermectin to be delivered. Taking into account the fact that a significant volume of use of ivermectin is in protecting and treating animals intended for slaughter for human consumption, there are constraints on the residual amount of active components such as ivermectin in the carcass of such an animal. Therefore, high loadings of ivermectin, even if technically feasible, in a delivery system are not necessarily the optimum solution.

Combination formulations are also desirable taking account of acquired tolerance or resistance in pests to prolonged usage of other more traditional parasiticidal agents. This phenomenon is well documented, e.g. in relation to worming compositions. Synergistic effects or complementary effects of combined parasiticidal agents have been observed as a route to combating the aforesaid tolerance problem. Synergistic anthelmintic compositions are discussed in WO 94/28887, which focuses on substituted mono- and bisphenols, salicylanilides, benzene sulphonamides, halogenated be benzimidazoles, benzimidazoles, and benzimidazole carbamates.

The opportunity to combine the use of avermectins with other parasiticidal agents has been explored already. Thus one finds that skin-absorbable pour-on formulations containing triclabendazole, optionally containing an avermectin, tetramisole or levamisole have been proposed in WO 0061068. An injectable formulation containing closantel together with an avermectin or milbemycin has been proposed in WO 95/05812. Formulations of the pour-on and injectable type are suggested in WO 01/60380, which comprise use of a pyrrolidone solvent and a bridging solvent such as a xylene, optionally including a further solubility agent such as propylene glycol caprylic acids and esters or peanut oil. This special solvent system is needed to address the difficulties of formulating differing parasiticidal agents such as closantel and ivermectin together. No disclosure of the efficacy of these formulations is made.

Other non-aqueous pour-on formulations are disclosed in WO97/13508, using a range of solvents, particularly polyalcohols, their ethers and mixtures thereof, optionally in combination with various co-solvents. Whilst that reference does present results of trials of formulations disclosed therein they show limited success in achieving transfer of the active components into the bloodstream of the treated animal as discussed hereafter in the comparative Example.

Salicylanilide derivatives such as closantel provide useful control over a range of parasites and are especially useful against liver fluke. The avermectin group of anti-parasitic compounds of which ivermectin is the best known example, provide complementary protection against many other parasites such as roundworms. Therefore, there are advantages to be gained if a combination of these drugs could be provided in a form that can be conveniently administered to livestock and which will provide effective control of parasitic infection.

In particular the provision of an effective pour-on formulation containing closantel and ivermectin is therefore a highly desirable goal. The provision of a satisfactory formulation is problematical because the solubility regime for each drug is different. An alkaline system provides the optimum pH for closantel, whereas ivermectin requires an acidic medium for satisfactory dissolution.

OBJECTS OF THE INVENTION

It is an object of the present invention to provide improved veterinary pharmaceutical preparations. In particular it is an object of the invention to provide a composition having activity against a broad range of endo- and ectoparasites including flukes. It is a further object of this invention to provide preparations that are suitable for topical administration, preferably presenting dosantel as a pour-on formulation. A still further object of the invention is to provide a veterinary pharmaceutical product combining closantel and ivermectin In an effective formulation enabling enhanced bioavailability of closantel in excess of those known in the prior art.

SUMMARY OF THE INVENTION

Surprisingly it has been found that a salicylanilide, optionally with another anthelmintic, can be dissolved in one or more alcohols and that this formulation is useful as a "pour-on" formulation that provides efficacious levels of the salicylanilide, and the other anthelmintic, in the blood of an animal when it is topically applied to the skin of the animal over a pre-determined period of time.

Accordingly, the invention enables the provision of effective pour-on parasiticidal compositions, especially combination products, containing closantel or the like salicylanilides, particularly binary formulations based on a salicylanilide together with another parasiticidal agent, for example of the avermectin or milbemycin type, with effective bioavailability of the parasiticidal agents.

The inclusion of a polymeric moiety can enhance the efficacy of a pour-on parasiticidal composition of the present invention. One suitable polymeric moiety is polyethylene glycol (PEG) or a polyvinylpyrrolidone (PVP), but other polymeric moieties may be used, e.g. a polyoxypropylene/polyoxyethylene block copolymer (poloxamer). Combinations of these polymeric moieties are also contemplated for the implementation of the invention described herein. The amounts thereof are variable, but from at least 0.1% (w/v) and up to 35% (w/v) or more of the polymeric moiety should be considered, with an amount of about 20% (w/v) being preferred.

It is considered that the presence of a polymeric moiety, like PEG, increases the level of closantel that can be dissolved in the pour-on formulation of the present invention.

According to a first aspect of the invention, a salicylanilide, especially closantel but also other salicylanilides including niclosamide, oxyclozanide, and rafoxanide, is presented in a pour-on formulation characterized by the presence of a delivery system comprising at least 20% v/v of one or more alcohols.

lower alkanols ($C_1$-$C_6$). The most preferred delivery system comprises at least 20% v/v ethanol with isopropanol being additionally used to bring the formulation to 100% v/v for use.

Typically the delivery system of this particular invention further comprises a polymeric moiety selected from polyethylene glycol (PEG), polyvinylpyrrolidone (PVP) and polyoxypropylene/polyoxyethylene block copolymers (poloxamers). When the delivery system comprises PEG, PVP, or a poloxamer, it is found that this provides pour-on formulations offering additional permeation of the active component(s)

through the skin thus increasing the available amount of active drug in the plasma of the treated subject.

The delivery system may be made up for use with typical formulation auxiliaries such as surfactants, embittering denaturants (anti-licking), preservatives, spreading aids penetration or occlusion enhancers, and anti-oxidants, e.g. butylated hydroxy toluene (BHT), butylated hydroxy anisole (BHA), or sodium formaldehyde-sulphoxylate.

According to another aspect of the invention, a parasiticidal composition comprises a first parasiticidal agent selected from amongst the salicylanilides, together with another parasiticidal agent selected from the avermectins and the milbemycins, in a delivery system comprising at least 20% v/v of one or more alcohols. The delivery system may include primary, secondary, tertiary and aromatic alcohols. The preferred alcohols are monohydric aliphatic or aromatic alcohols, more preferably lower alkanols ($C_1$-$C_6$). The most preferred delivery system comprises at least 20% v/v ethanol with isopropanol being additionally used to bring the formulation to 100% v/v for use. Typically the solution of this particular invention further comprises a polymeric moiety selected from polyethylene glycol (PEG), polyvinylpyrrolidone (PVP) and polyoxypropylene/polyoxyethylene block copolymers (poloxamers).

Thus use of an alcohol e.g. ethanol alone or in combination with isopropanol and/or a polymeric moiety such as PEG, PVP or a poloxamer is found to be effective in the manufacture of a pour-on parasiticidal composition comprising closantel having long acting efficacy, such that the amount of polymeric moiety used enables the desired period of efficacy to be designed into the formulation to provide a controllable period of effective treatment whilst still permitting slaughter for human consumption of the treated animal if required having regard to the legally prescribed withdrawal period. The polymeric moiety maintains the solubility of closantel in the delivery system, especially in the presence of water. Further, the use of a polymeric moiety such as PEG or PVP does not inhibit the bioavailability of an avermectin such as ivermectin present in a formulation according to the invention, showing that pour-on formulations, comprising a polymeric moiety e.g. PVP, poloxamer, PEG, or a combination thereof can be used for the effective delivery of active ingredients of a diverse nature and will therefore be likely to find wide utility in the field of animal health.

A suitable delivery system comprises a solvent and co-solvent(s) selected from the group consisting of aliphatic and aromatic alcohols, i.e. primary, secondary, tertiary and aromatic alcohols. The preferred alcohols are monohydric aliphatic or aromatic alcohols, more preferably lower alkanols ($C_1$-$C_6$). The most preferred delivery system comprises at least 20% v/v ethanol with isopropanol being additionally used to bring the formulation to 100% v/v for use. Preferably, one of said alcohols is ethanol present in an amount of at least 20% v/v and another alcohol is isopropanol which can be used to bring the solution up to 100% v/v for use.

Alternatively the delivery system comprises a lower aliphatic alcohol such as ethanol with a glycol solvent such as a PEG solvent, to which is added isopropanol to bring the solution to 100% (v/v) for use.

A range of PEG solvents according to molecular weight is commercially available, and any of those, or others that may yet be made available, may be chosen for convenience provided that the PEG is presented or rendered available as a liquid during formulation. Typically, PEG 200 to 6000 are readily to hand from commercial sources, and thus can be used for the purposes herein, but PEG 200 to PEG 600 are usefully employed in this invention. A preferred delivery system comprises the solvents PEG 200 with ethanol and isopropanol, together with a polymeric moiety (e.g. PVP) to enhance permeability.

A proportion of the PVP may be substituted by higher molecular weight polyethylene glycols, up to a molecular weight of 20000.

Thus according to the invention, it is now possible to obtain in a single pour-on formulation, a salicylanilide, preferably but not restricted to closantel, and an avermectin, preferably ivermectin, which is effective to deliver closantel when administered to an animal such that an effective plasma concentration of both closantel or another salicylanilide and ivermectin is readily achieved. Examples of salicylanilides other than closantel that could be utilized include, but are not restricted to, niclosamide, oxyclozamide, and rafoxanide. Of course formulations containing just one of these active ingredients can be utilised if desired for clinical reasons.

formulations are:
Closantel—from 1 to 30% w/v, preferably 1 to 15% w/v.;
Ivermectin—from 0.1 to 10% w/v, preferably 0.1 to 5% w/v;
For other salicylanilides, the range of 1 to 30% w/v, preferably 1 to 15% w/v would be applicable.

The quantity of polymeric moiety, especially PEG required to be effective depends on the desired salicylanilide activity of the mixture but preferably at least 3% (w/v) PEG, more preferably 20% (w/v) is used to permit the higher effective amounts of e.g. closantel desired to be achieved. The amount of polymeric material used is only limited by the amount of alcohol used in the delivery system, and thus could be up to 80% v/v.

DESCRIPTION OF THE DRAWING

The accompanying single FIGURE drawing referred to hereinafter illustrates, by way of a graph, a comparison of pharmacokinetic profile of a formulation of the invention with a commercially available product.

MODES FOR CARRYING OUT THE INVENTION

The invention will now be further described by way of illustrative example according to the best modes currently known.

Formulation Examples

In the preparation of a binary combination product for delivery in a pour-on presentation, the active components closantel and ivermectin were provided in amounts to deliver 10% (w/v) closantel and 0.5% (w/v) ivermectin. The delivery systems used included the solvents PEG 200, ethanol and isopropyl alcohol which readily provided for effective salvation of the actives, together with a permeability enhancer, the compositions of several illustrative formulations are as follows:

| Formulation 1 | |
|---|---|
| Ivermectin | 0.25% w/v |
| Closantel | 5.0% w/v |
| Ethanol | 30% v/v |
| Isopropyl Alcohol to | 100% v/v |
| Formulation 2 | |
| Ivermectin | 0.5% w/v |
| Closantel (as Na salt) | 10.0% w/v |

-continued

| | |
|---|---|
| PVP | 15.0% w/v |
| Ethanol | 20% v/v |
| PEG 200 | 20% v/v |
| Isopropyl Alcohol | to 100% v/v |

Formulation 3

| | |
|---|---|
| Ivermectin | 0.5% w/v |
| Closantel | 10% w/v |
| PVP | 6% w/v |
| Crodamol CAP (emollient ester mix) | 10% w/v |
| Tributyl Citrate | 0.3% w/v |
| Polyethylene Glycol 200 | 20% v/v |
| Ethanol | 20% v/v |
| Denatonium Benzoate | 0.05% w/v |
| Isopropyl alcohol | q.s. to 100% |

General Method of Formulation:

These formulations were made up following usual industry practice.

Administration Example

The formulations (1, 2 and 3) made as described above were presented for administration according to accepted industry procedures and the testing thereof is presented below.

The formulation containing closantel and ivermectin according to the above compositions (formulation 1, 2 and 3) were applied to cattle at an ivermectin-does rate equivalent to 500 µg/kg of bodyweight, and a closantel-dose rate of 10 mg/kg of bodyweight.

The blood plasma results for closantel are shown in Tables 1, 4 and 5 and for ivermectin in Tables 2, 3 and 6.

TABLE 1

Plasma Levels of Closantel (µg/ml) after Pour on Administration of Formulation 1 at a dose rate of 10 mg/kg bodyweight on one occasion

| | Closantel | |
|---|---|---|
| Hours | Mean | SEM |
| 24 | 2.0 | 1.21 |
| 48 | 10.3 | 3.57 |
| 60 | 14.44 | 4.75 |
| 72 | 18.18 | 5.6 |
| 80 | 19.63 | 6.01 |
| 96 | 21.57 | 6.46 |
| 120 | 22.10 | 6.53 |
| 168 | 24.98 | 7.28 |
| 240 | 26.96 | 7.53 |

TABLE 2

Plasma levels of Ivermectin (ng/ml) in Cattle after pour-on administration of Formulation 1 at a dose rate of 500 µg/kg bodyweight on 1 occasion

| | Ivermectin | |
|---|---|---|
| Hours | Mean | SEM |
| 24 | 4.95 | 1.14 |
| 48 | 14.53 | 3.49 |
| 60 | 16.60 | 5.44 |
| 72 | 19.11 | 6.23 |
| 80 | 19.94 | 6.19 |
| 96 | 19.73 | 6.41 |
| 120 | 18.27 | 5.61 |
| 168 | 16.18 | 5.03 |
| 240 | 10.55 | 3.23 |

TABLE 3

Plasma levels of Ivermectin (ng/ml) in Cattle after pour-on administration of Formulation 2 at a dose rate of 500 µg/kg bodyweight on 1 occasion

| Hours | Mean | SEM |
|---|---|---|
| 24 | 19.19 | 14.91 |
| 48 | 19.45 | 12.56 |
| 72 | 13.84 | 6.82 |
| 96 | 11.98 | 5.32 |
| 120 | 9.48 | 3.79 |
| 144 | 7.77 | 3.28 |
| 168 | 6.38 | 2.47 |
| 192 | 4.96 | 2.02 |
| 216 | 3.97 | 1.31 |
| 240 | 3.95 | 1.22 |
| 264 | 3.22 | 1.07 |

TABLE 4

Plasma Levels of Closantel (µg/ml) after Pour on Administration of Formulation 2 at a dose rate of 10 mg/kg bodyweight on one occasion

| Hours | Mean | SEM |
|---|---|---|
| 24 | 5.45 | 1.65 |
| 48 | 40.80 | 22.31 |
| 72 | 48.60 | 25.01 |
| 96 | 49.03 | 24.07 |
| 120 | 49.27 | 22.88 |
| 144 | 47.07 | 23.36 |
| 168 | 46.53 | 21.77 |
| 192 | 51.47 | 27.06 |
| 216 | 50.43 | 29.37 |
| 240 | 50.17 | 26.79 |
| 264 | 25.85 | 11.06 |

TABLE 5

Plasma levels of Closantel (µg/ml) after Pour on Administration of Formulation 3 at a dose rate of 10 mg/kg bodyweight on one occasion

| Hours | Mean | SEM |
|---|---|---|
| 24 | 36.2 | 12.2 |
| 48 | 42.8 | 23.4 |
| 54 | 43.8 | 23.6 |
| 72 | 52.2 | 29 |
| 78 | 55.6 | 30.2 |
| 96 | 47.2 | 24.6 |
| 120 | 45.4 | 22.6 |
| 192 | 39 | 20.2 |
| 240 | 34.6 | 10.4 |

TABLE 6

Plasma levels of Ivermectin (ng/ml) in Cattle after pour-on administration of Formulation 3 at a dose rate of 500 µg/kg bodyweight on 1 occasion

| Hours | Mean | SEM |
|---|---|---|
| 24 | 15.64 | 4.54 |
| 48 | 28.76 | 8.84 |
| 54 | 25.40 | 6.70 |
| 72 | 19.79 | 4.68 |
| 78 | 17.89 | 4.07 |
| 96 | 15.25 | 3.90 |
| 120 | 12.75 | 1.59 |
| 192 | 7.88 | 1.43 |
| 240 | 6.22 | 1.21 |

From Tables 2, 3 and 6 it can be seen that the plasma levels achieved for ivermectin are suitable for the treatment of cattle in that they achieve levels of ivermectin similar to those obtained using a commercially available (ivermectin only) product.

Form Tables 1, 4 and 5 it is noted that the closantel levels achieved are those that are desired for a clinically effective product given that plasma concentration is crucial for the clinical flukicidal efficacy of the product. It is known that successful flukicidal activity is based upon the plasma concentration of the flukicide—as the plasma concentration increases the age of the fluke that can be exterminated decreases therefore increasing the possibility of a complete cure. With the closantel plasma concentrations demonstrated in Table 1, 4 and 5, it would be surmised that the formulation of the Norbrook invention would be effective against both adult and immature fluke.

Effective amounts of a salicylanilide would be that amount of the drug in the pour on formulation sufficient to provide efficacious blood plasma levels, about 40-50 μg/ml blood plasma. Therefore, the effective amount is the amount that provides efficacy against the target parasite, especially liver fluke. An effective dose rate for closantel is ~10 mg closantel per kg body weight, and for other salicylanilides such as niclosamide, oxyclozanide, and rafoxanide is likely to be in the range of 10 to 12 mg per kg of body weight.

The results obtained for closantel are also notably superior to those obtained in WO 97/13508 wherein a topical dose rate of 10 mg/kg closantel produced a maximum blood plasma level of only 8.37 μg/ml (at 10 days). The formulations of that application required a dose of 40 mg/kg in order to achieve a blood plasma level of 52.97 μg/mL. The results from that document for a 10 mg/kg dose are compared graphically with those of Table 4 In the FIGURE. It can be clearly seen that the formulation of the Norbrook invention provides for a vastly superior pharmacokinetic profile in terms of maximum concentration and in duration of activity indicating that the Norbrook invention would provide for a product with superior clinical efficacy against flukes of all stages. In order to achieve such a profile the formulation of WO 97/13508 had to be administered at 40 mg/kg—such a very high dose rate of closantel, in order to achieve desirable plasma levels, poses a high risk of toxicity to the animal thus negating the pharmacokinetic profile. Therefore it can be seen that the compositions according to the present invention are surprisingly superior to the known art.

INDUSTRIAL APPLICABILITY

In view of the aforesaid advantages and properties of the compositions described herein, the invention will be usefully applied in the field of veterinary medicine in particular for combating endoparasites and ectoparasites typically afflicting livestock such as bovines, equines, ovines and caprines.

The invention claimed is:

1. An anti-parasitic pour-on composition comprising
   (a) a delivery system for absorption through the skin;
   (b) a therapeutically effective amount of a salicylanilide anti-parasitic compound, wherein the salicylanilide is closantel or a pharmaceutically acceptable salt thereof; and
   (c) an effective amount of at least one other anti-parasitic compound selected from the group consisting of avermectins and milbemycins; and
   said delivery system comprising at least 20% (v/v) of one or more monohydric C1-C6 alcohols and said composition being substantially free of 2-pyrrolidone and N-methyl-2-pyrrolidone.

2. A composition according to claim 1, wherein closantel is present in an amount of 1 to 30% (w/v).

3. A composition according to claim 1, wherein the other antiparasitic compound is ivermectin.

4. A composition according to claim 3, wherein ivermectin is present in an amount in the range 0.1 to 10% (w/v).

5. A composition according to claim 1, wherein the one or more monohydric C1-C6 alcohols comprises alcohols selected from the group consisting of primary, secondary, and tertiary aliphatic alcohols.

6. A composition according to claim 1, wherein the delivery system also comprises at least one of the following auxiliaries: surfactants, embittering denaturants (anti-licking), preservatives, spreading aids, penetration or occlusion enhancers, and antioxidants.

7. A composition according to claim 1, wherein the delivery system additionally comprises up to 35% (v/v) of a polymeric moiety.

8. A composition according to claim 7, wherein the polymeric moiety is selected from the group consisting of polyethylene glycol (PEG), polyvinyl pyrrolidone (PVP) and polyoxypropylene/polyoxyethylene block copolymers.

9. A composition according to claim 8, wherein the polymeric moiety is present in an amount in the range of from 3% (w/v) to 20% (w/v).

10. A composition according to claim 7, wherein the delivery system comprises polyethylene glycol, isopropyl alcohol and at least 20% ethanol.

11. A composition according to claim 8, wherein the polymeric moiety is polyvinyl pyrrolidone.

12. A composition according to claim 1, wherein said one or more monohydric C1-C6 alcohols in the delivery system consists of a mixture of ethanol and isopropyl alcohol comprising at least 20% ethanol (v/v).

13. A composition according to claim 7, wherein the delivery system also comprises at least one of the following auxiliaries: surfactants, embittering denaturants (anti-licking), preservatives, spreading aids, penetration or occlusion enhancers, and antioxidants.

14. A method for killing flukes comprising topically applying to a mammal parasitized by flukes an anti-parasitic pour-on composition, said composition comprising:
   (a) a delivery system for absorption through the skin;
   (b) a therapeutically effective amount of a salicylanilide anti-parasitic compound; and
   (c) an effective amount of at least one other anti-parasitic compound;
   said delivery system comprising at least 20% (v/v) of one or more monohydric C1-C6 alcohols and said composition being substantially free of 2-pyrrolidone and N-methyl-2-pyrrolidone.

15. A method for killing flukes comprising topically applying to a mammal parasitized by flukes a composition comprising:
   (a) a delivery system for absorption through the skin;
   (b) a therapeutically effective amount of a salicylanilide anti-parasitic compound; and
   (c) an effective amount of at least one other anti-parasitic compound;
   said delivery system comprising at least 20% (v/v) of one or more monohydric C1-C6 alcohols, and up to 35% (v/v) of a polymeric moiety, and said composition being substantially free of 2-pyrrolidone and N-methyl-2-pyrrolidone.

* * * * *